(12) United States Patent
Noble et al.

(10) Patent No.: US 12,171,889 B1
(45) Date of Patent: Dec. 24, 2024

(54) SHORT-WAVE LENGTH, ULTRAVIOLET LIGHT MACHINE USING GREEN ENERGY

(71) Applicants: Latesha Noble, Chula Vista, CA (US); Adesola Akindele, London (GB); Adnan Ghoury Javed, Lahore Cantt (PK)

(72) Inventors: Latesha Noble, Chula Vista, CA (US); Adesola Akindele, London (GB); Adnan Ghoury Javed, Lahore Cantt (PK)

(73) Assignee: HYGEAR TECHNOLOGIES, INC., Chula Vista, CA (US)

(*) Notice: Subject to any disclaimer, the term of this patent is extended or adjusted under 35 U.S.C. 154(b) by 667 days.

(21) Appl. No.: 17/319,958

(22) Filed: May 13, 2021

Related U.S. Application Data

(60) Provisional application No. 63/024,310, filed on May 13, 2020.

(51) Int. Cl.
| | | |
|---|---|---|
| *A61L 2/10* | (2006.01) | |
| *A61L 2/00* | (2006.01) | |
| *A61L 9/20* | (2006.01) | |
| *F21L 4/08* | (2006.01) | |
| *F21V 23/04* | (2006.01) | |
| *F21Y 115/10* | (2016.01) | |

(52) U.S. Cl.
CPC .......... *A61L 2/0047* (2013.01); *A61L 2/00* (2013.01); *A61L 2/10* (2013.01); *A61L 9/20* (2013.01); *F21L 4/08* (2013.01); *F21V 23/0471* (2013.01); *A61L 2202/11* (2013.01); *A61L 2202/14* (2013.01); *A61L 2209/111* (2013.01); *A61L 2209/12* (2013.01); *F21Y 2115/10* (2016.08)

(58) Field of Classification Search
CPC ........................................................ A61L 2/10
See application file for complete search history.

(56) References Cited

U.S. PATENT DOCUMENTS

2005/0258108 A1* 11/2005 Sanford .................. C02F 1/325
  210/748.11
2020/0261608 A1* 8/2020 Crosby ................. A61L 2/0047

* cited by examiner

*Primary Examiner* — Kevin Joyner
(74) *Attorney, Agent, or Firm* — Plager Schack LLP; Mark H. Plager, Esq.; Michael J. O'Brien, Esq.

(57) ABSTRACT

A short wave ultraviolet light machine is configured to disrupt microbes. The machine has a housing having an outer shell and a hollow inner portion. A solar panel is joined to the outer shell and electrically coupled to a battery charge controller within the hollow inner portion. A lithium polymer energy storage device is arranged within the hollow inner portion and is electrically coupled to the battery charge controller. A short-wave ultraviolet light emitting diode module is arranged on the outer shell and electrically coupled to the battery charge controller with an electronic controller module. A proximity sensor module is arranged on the outer shell and electrically coupled to the electronic controller module. The proximity sensor detects a surface and engages the short-wave ultraviolet light emitting diode module to emit a short wave ultraviolet light that disrupts microbes proximate the short wave ultraviolet light emitting diode machine.

3 Claims, 5 Drawing Sheets

SHORT-WAVE LENGTH, ULTRAVIOLET LIGHT MACHINE USING GREEN ENERGY

RELATED APPLICATION

This application claims priority to provisional patent application U.S. Ser. No. 63/024,310 filed on May 13, 2020, the entire contents of which is herein incorporated by reference.

BACKGROUND

The embodiments herein relate generally to antimicrobial devices.

Viruses do not reproduce on their own, but they do have genetic material. During the Covid-19 pandemic in 2019, DNA effective virus protection, personal protection, sanitizing and disinfection products were scarce. This was due to an increased simultaneous global demand leading to the lack of resources and a fractured global supply network. Added quarantine, shelter-in-place and curfew measures worldwide have affected human capital capacities in manufacturing locations of the products used to protect and sanitize.

Prior to embodiments of the disclosed invention, convenient and efficient methods to do this continuously without needing added replacements or plug in power source including cartridges or refill mechanisms, as well, safe ways to discard these items used were lacking. Further, there is a need to reveal germs in dim lighting. Embodiments of the disclosed invention solve this problem.

SUMMARY

A short wave ultraviolet light machine is configured to disrupt microbes. The machine has a housing having an outer shell and a hollow inner portion. A solar panel is joined to the outer shell and electrically coupled to a battery charge controller within the hollow inner portion. A lithium polymer energy storage device is arranged within the hollow inner portion and is electrically coupled to the battery charge controller. A short-wave ultraviolet light emitting diode module is arranged on the outer shell and electrically coupled to the battery charge controller with an electronic controller module. A proximity sensor module is arranged on the outer shell and electrically coupled to the electronic controller module. The proximity sensor detects a surface and engages the short-wave ultraviolet light emitting diode module to emit a short wave ultraviolet light that disrupts microbes proximate the short wave ultraviolet light emitting diode machine.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

By way of example, and referring to FIGS. 1-4, one embodiment of a short wave ultraviolet light machine further comprises a 555 timer circuit further comprising a ground pin attached to ground and a voltage source. A trigger pin is attached to the voltage source and a ground with a switch and a resister. An output pin is attached to ground with a capacitor and to a control pin on an LED driver integrated circuit. A voltage pin is attached to the voltage source. A discharge pin is attached to the voltage source with a resister and to ground with a capacitor.

The LED driver integrated circuit has a voltage input pin and a switching node attached to the negative lead on a UVC LED. The feedback pin is attached to the positive lead of the UVC LED. The output error amplified and ground pin are both attached to ground. An example of the LED driver integrated circuit is the TPS61165 High-Brightness, White LED Driver.

The voltage source can be a battery and the battery can be a lithium polymer energy storage device. The voltage source can be attached to a charge management controller such as the Microchip MCP73831 Single Cell, Li-Ion/Li-Polymer Charge Management Controller. The charge management controller has a supply voltage pin attached to a supply voltage pin and a ground pin on a battery charge source. A program pin is attached to a pair of light emitting diodes, the ground, and a status pin. A voltage battery pin is attached to the charge pin on a battery, and the charge source for the components listed above.

Figure 1:
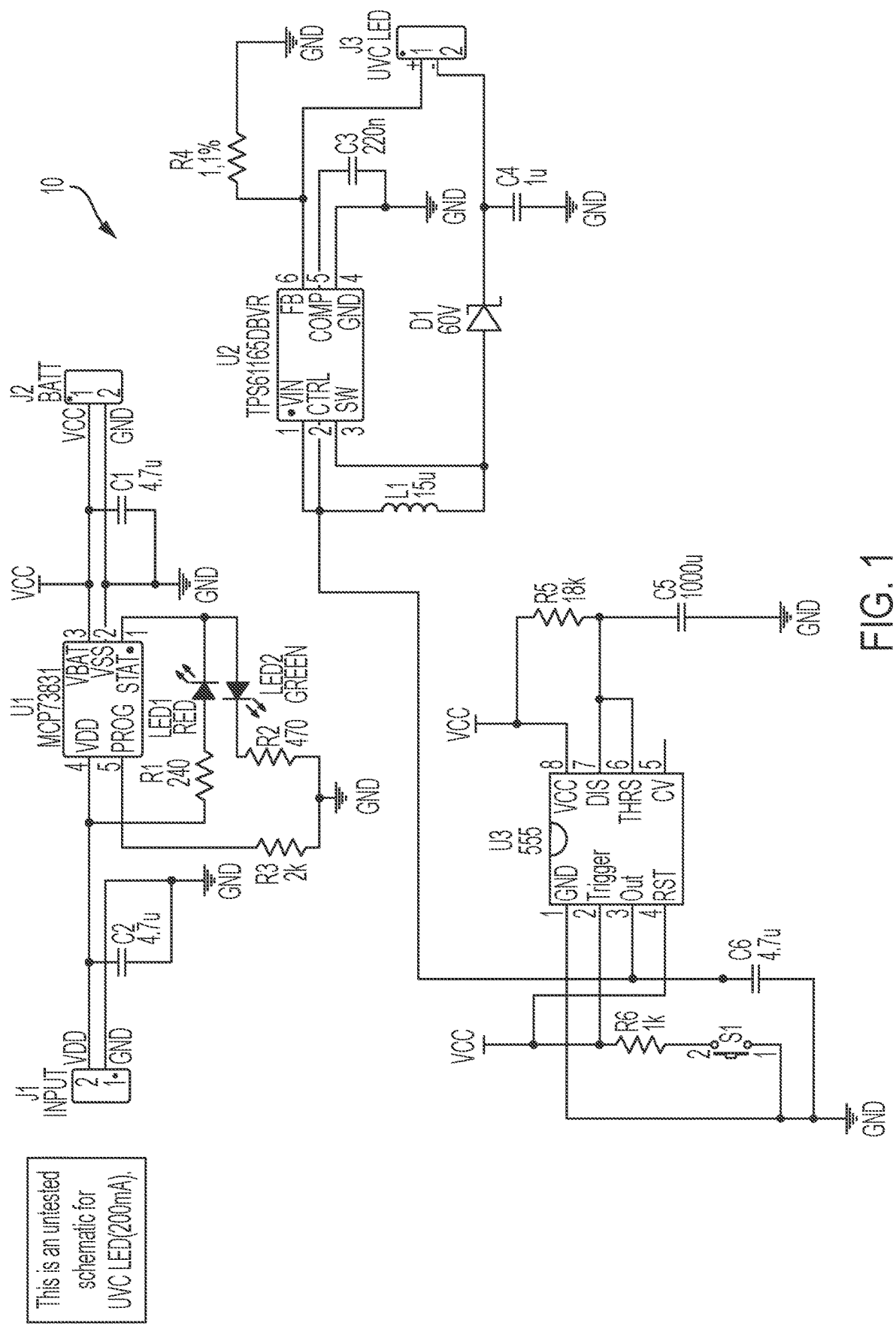
FIG. 1 shows an electrical schematic view of one embodiment of the present invention.
Figure 2A:
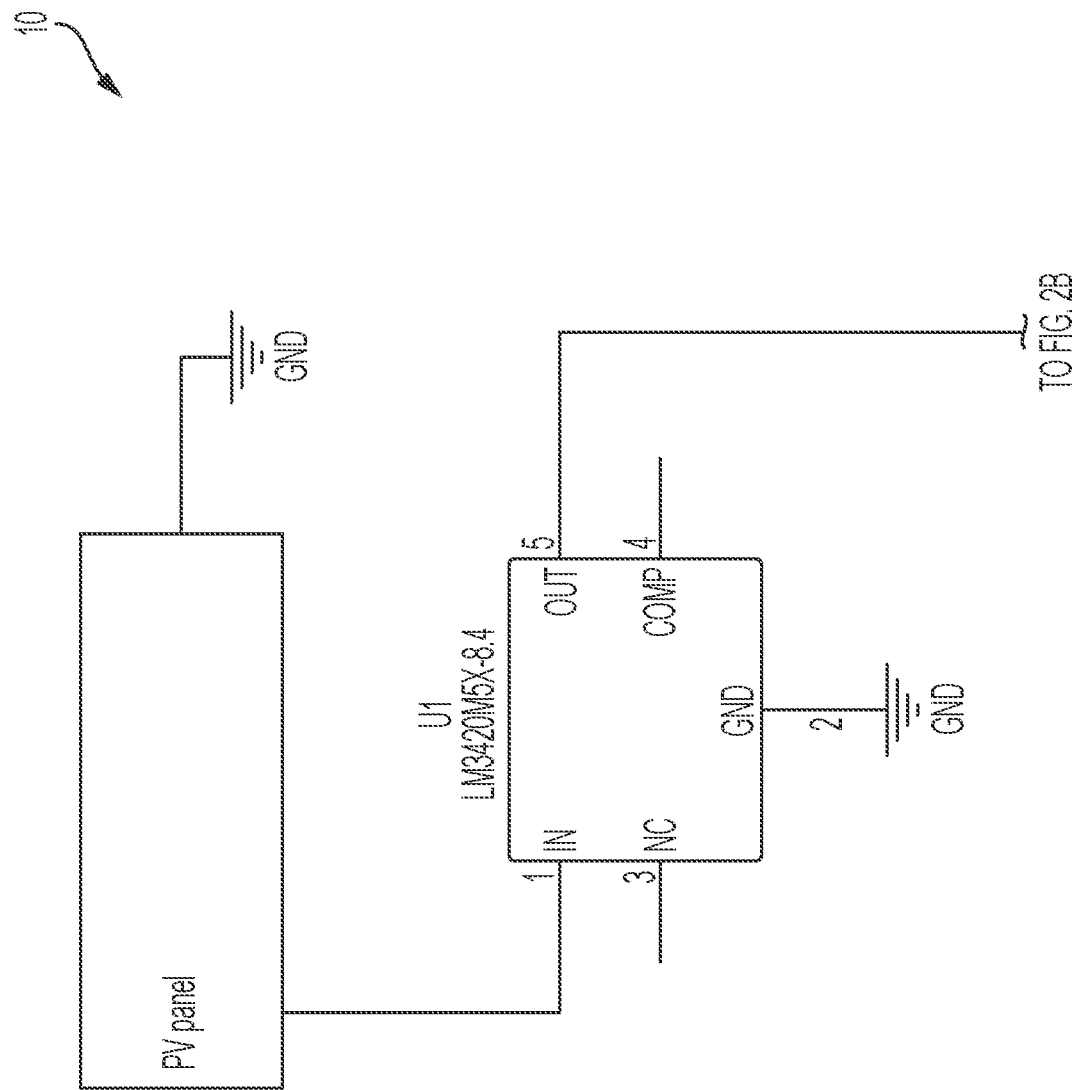
FIG. 2A shows an electrical schematic view of one embodiment of the present invention.
Figure 2B:
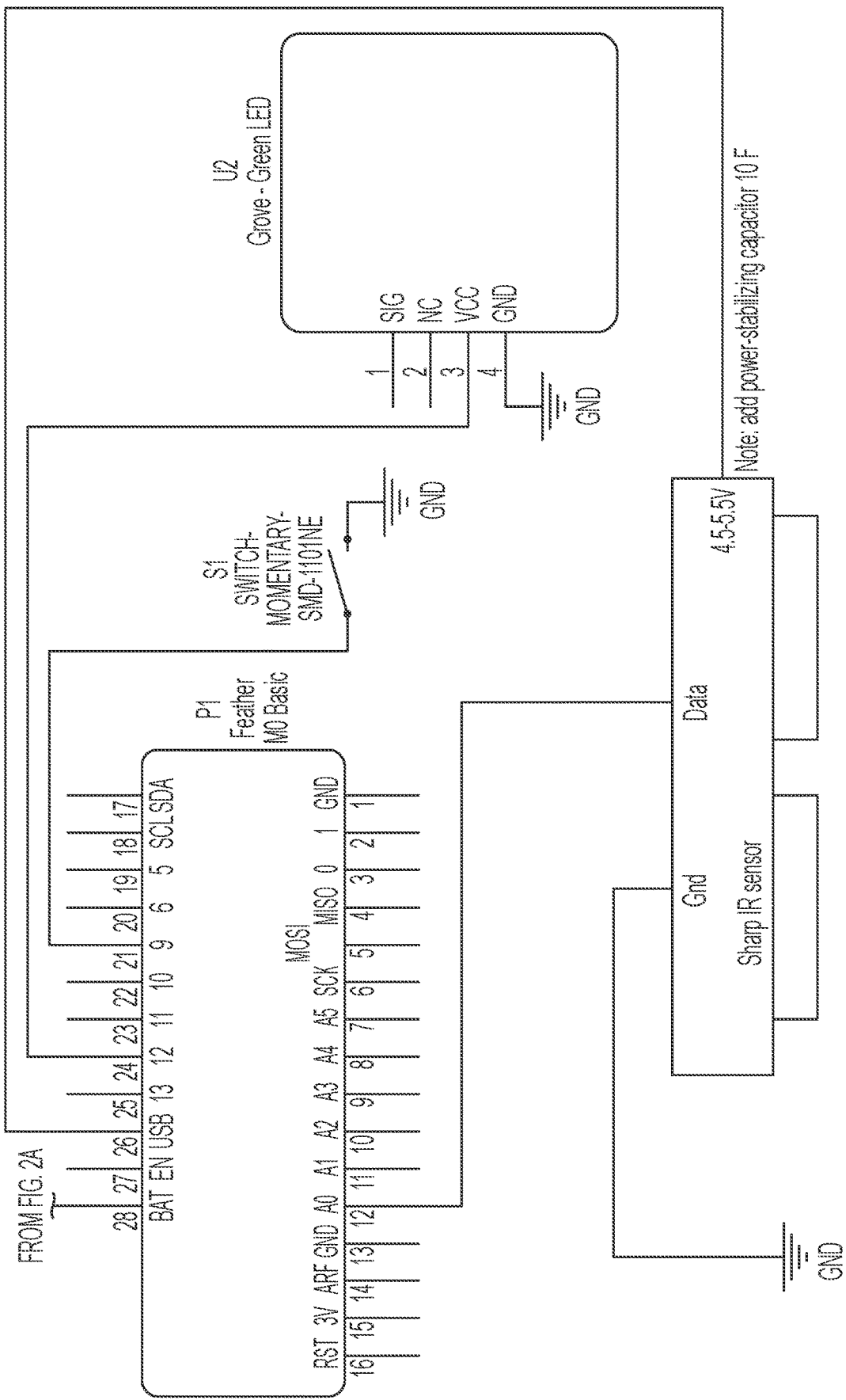
FIG. 2B shows an electrical schematic view of one embodiment of the present invention.

There can be a second voltage source going into a charge controller as shown in FIG. 2A. A battery charge controller, such at the Texas Instruments LM3420M5X-8.4/NOPB, is electrically coupled to a photovoltaic panel. A charge controller output pin is electrically coupled to a development board. The development board can be an Adafruit Feather M0 Basic Proto. The development board is electrically coupled to a grove green light emitting diode and an infrared sensor.

Figure 3:
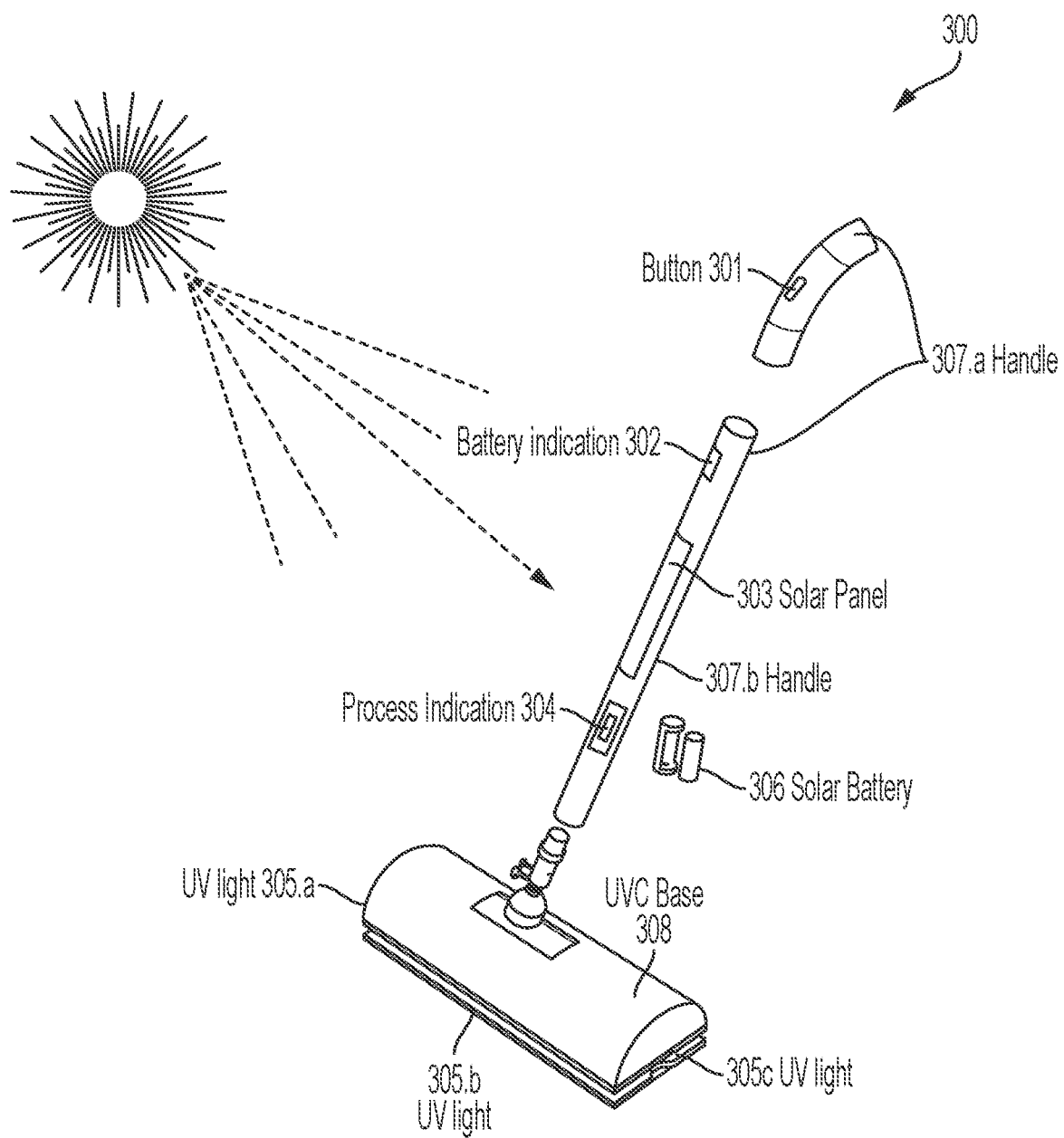
FIG. 3 shows a perspective view of one embodiment of the present invention.

Turning to FIG. 3, one embodiment of short-wave length, ultraviolet light machine 300 further comprises a button 301 arranged on a handle 307a. The handle 307a is joined to a handle 307b. further comprises a batter indicator 302, a solar panel 303, and a process indication 304. Solar battery 306 can be inserted into the handle 307b and charged by the solar panel 303 as explained above. The handle 307b is attached to a UVC Base 308 having a first UV light 305a, a second UV light 305b, and a third UV light 305c.

Figure 4:
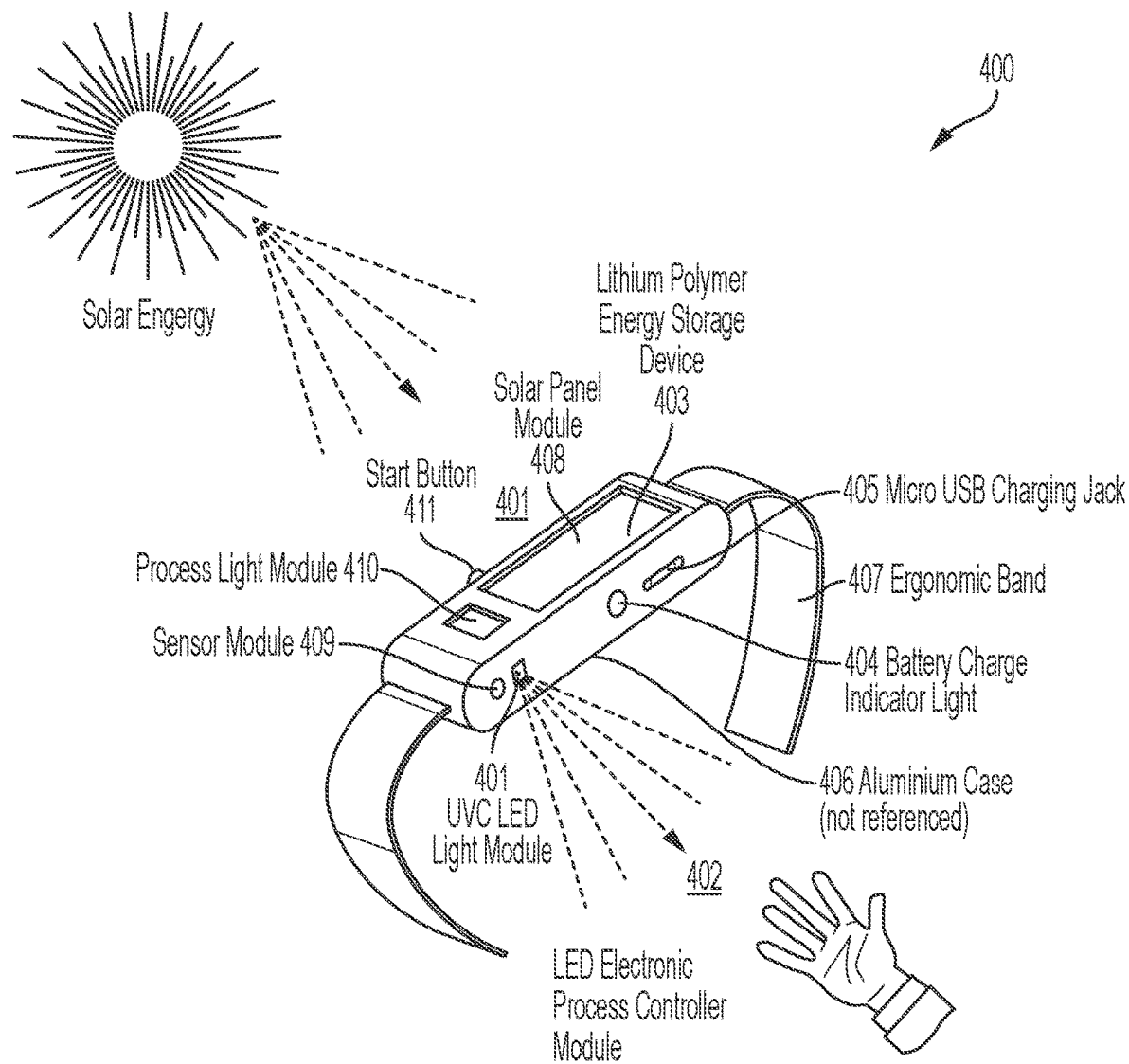
FIG. 4 shows a perspective view of one embodiment of the present invention.

Turning to FIG. 4, one embodiment of short-wave length, ultraviolet light machine 400 further comprises a UVC LED module 401 which provides UVC light 402. The UVC LED module 401 is arranged on an aluminum casing 406 have a lithium polymer energy storage device 403, a micro-USB charging jack 405, an ergonomic band 407, a solar panel module 408, a sensor module 409, and a process light module 410.

In some embodiments, a battery charge indicator light is mechanically coupled to the outer shell and electrically coupled to the battery charge controller module. The battery charge indicator light indicates a state of charge of the lithium polymer energy storage device.

The solar panel absorbs rays from the Sun. The lithium solar batteries work by storing energy produced by your solar panels and storing it as for later use. In some cases, solar batteries have their own inverter and offer integrated energy conversions which will be an option for larger devices.

The mechanism action mode will be basic and intuitive, which is activated by the sensor module. The ultraviolet light will only turn on when the short wave ultraviolet light emitting diode module is exposed against the surface and when nothing is in front of it, it will turn off automatically as a safety feature. Upon detecting a surface, the idle yellow light will turn blue as to indicate the disinfection process only when the device is the optimum proximity to the surface that needs to be sanitized and finally upon completion within the required time, short wave ultraviolet light emitting diode is turned off with the indication light turning green.

The machine can be used in multiple devices as varied sizes as follows: a miniature version in a wearable bracelet and pendant, protection eye wear, a medium size fitted in a mop casing, be a mop or steam mop attachment, a handheld household wand, a large size as a heating ventilation and air conditioning filter, a vacuum cleaner attachment, a flexi-fabric sanitation clothing and self-sanitizing gloves.

The machine can also be used as a protective layer in space suits. It can also be used as an added disinfecting layer for heating, ventilation and air conditioning system in household, commercial, transportation (air, land, on-the-water, under-the-sea, space) and space stations.

As used in this application, the term "a" or "an" means "at least one" or "one or more."

As used in this application, the term "about" or "approximately" refers to a range of values within plus or minus 10% of the specified number.

As used in this application, the term "substantially" means that the actual value is within about 10% of the actual desired value, particularly within about 5% of the actual desired value and especially within about 1% of the actual desired value of any variable, element or limit set forth herein.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Any element in a claim that does not explicitly state "means for" performing a specified function, or "step for" performing a specified function, is not to be interpreted as a "means" or "step" clause as specified in 35 U.S.C. § 112, ¶ 6. In particular, any use of "step of" in the claims is not intended to invoke the provision of 35 U.S.C. § 112, ¶ 6.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A short wave ultraviolet light machine, configured to disrupt microbes; the machine comprising:
    a housing having an outer shell and a hollow inner portion;
    a solar panel joined to the outer shell and electrically coupled to a battery charge controller within the hollow inner portion;
    a lithium polymer energy storage device, arranged within the hollow inner portion and electrically coupled to the battery charge controller;
    short wave ultraviolet light emitting diode module, arranged on the outer shell and electrically coupled to the battery charge controller with an electronic controller module;
    a proximity sensor module, arranged on the outer shell and electrically coupled to the electronic controller module;
    a 555-timer circuit further comprising a ground pin attached to ground and the lithium polymer energy storage device;
    a trigger pin, attached to a voltage source and a ground with a switch and a resister;
    an output pin, attached to ground with a capacitor and to a control pin on an LED driver integrated circuit;
    a voltage pin is attached to the lithium polymer energy storage device;
    a discharge pin is attached to the lithium polymer energy storage device with a resister and to ground with a capacitor;
    wherein the proximity sensor detects a surface and engages the short-wave ultraviolet light emitting diode module to emit a short-wave ultraviolet light that disrupts microbes proximate the short-wave ultraviolet light machine.

2. A short wave ultraviolet light machine, configured to disrupt microbes; the machine comprising:
    a housing having an outer shell and a hollow inner portion;
    a solar panel joined to the outer shell and electrically coupled to a battery charge controller within the hollow inner portion;
    a lithium polymer energy storage device, arranged within the hollow inner portion and electrically coupled to the battery charge controller;
    short wave ultraviolet light emitting diode module, arranged on the outer shell and electrically coupled to the battery charge controller with an electronic controller module;
    a proximity sensor module, arranged on the outer shell and electrically coupled to the electronic controller module;
    a LED driver integrated circuit that further comprises:
    a voltage input pin and a switching node attached to a negative lead on a UVC LED;
    a feedback pin, attached to a positive lead of the UVC LED; and
    an output error amplified pin and ground pin, attached to ground;
    wherein the proximity sensor detects a surface and engages the short-wave ultraviolet light emitting diode module to emit a short-wave ultraviolet light that disrupts microbes proximate the short-wave ultraviolet light machine.

3. A short wave ultraviolet light machine, configured to disrupt microbes; the machine comprising:
- a housing having an outer shell and a hollow inner portion;
- a solar panel joined to the outer shell and electrically coupled to a battery charge controller within the hollow inner portion;
- a lithium polymer energy storage device, arranged within the hollow inner portion and electrically coupled to the battery charge controller;
- short wave ultraviolet light emitting diode module, arranged on the outer shell and electrically coupled to the battery charge controller with an electronic controller module;
- a proximity sensor module, arranged on the outer shell and electrically coupled to the electronic controller module;
- a charge management controller, electrically coupled to the lithium polymer energy storage device; the charge management controller further comprising:
  - a supply voltage pin attached to a supply voltage pin and a ground pin on a battery charge source;
  - a program pin, attached to a pair of light emitting diodes, the ground, and a status pin;
  - a voltage battery pin, attached to the charge pin on the lithium polymer energy storage device;
- wherein the proximity sensor detects a surface and engages the short-wave ultraviolet light emitting diode module to emit a short-wave ultraviolet light that disrupts microbes proximate the short-wave ultraviolet light machine.

\* \* \* \* \*